United States Patent
Valentini et al.

[11] Patent Number: 5,152,284
[45] Date of Patent: Oct. 6, 1992

[54] DISPOSABLE INHALER WITH PRE-PIERCED CAPSULE

[75] Inventors: Luigi Valentini; Giancarlo Ceschel, both of Milan, Italy

[73] Assignee: Phidea S.p.A., Milan, Italy

[21] Appl. No.: 707,226

[22] Filed: May 24, 1991

Related U.S. Application Data

[63] Continuation of Ser. No. 479,273, Feb. 13, 1990, abandoned.

[30] Foreign Application Priority Data

Feb. 23, 1989 [IT] Italy .................. 19540 A/89

[51] Int. Cl.⁵ .................................... A61M 15/00
[52] U.S. Cl. .................. 128/203.21; 128/203.23; 128/203.12; 128/203.15
[58] Field of Search .............. 128/203.15, 203.12, 128/203.21, 203.23

[56] References Cited

U.S. PATENT DOCUMENTS

| | | | |
|---|---|---|---|
| 2,517,482 | 8/1950 | Hall | 128/203.21 X |
| 3,507,277 | 4/1970 | Altounyan et al. | 128/203.21 X |
| 3,669,113 | 6/1972 | Altounyan | 128/203.15 |
| 3,837,341 | 9/1974 | Bell | 128/203.21 X |
| 3,888,253 | 6/1975 | Watt et al. | 128/203.21 X |
| 3,906,950 | 9/1975 | Cocozza | 128/203.21 X |
| 3,918,451 | 11/1975 | Steil | 128/203.21 X |
| 4,069,819 | 1/1978 | Valentini et al. | 128/203.23 |
| 4,105,027 | 8/1978 | Lundquist | 128/203.21 X |
| 4,206,758 | 6/1980 | Hallworth et al. | 128/203.21 X |

FOREIGN PATENT DOCUMENTS 07351  7/1990  World Int. Prop. O. ...... 128/203.15

*Primary Examiner*—Edgar S. Burr
*Assistant Examiner*—Eric P. Raciti
*Attorney, Agent, or Firm*—Fisher, Christen & Sabol

[57] ABSTRACT

A disposable inhaler (10; 50; 60) for administering medicaments in finely divided form contained in capsules (22) comprises a body (12) enclosing a nebulization chamber (20), the capsule being inserted into the nebulization chamber during assembly of the component parts of the inhaler. The inhaler does not comprise a device for piercing the capsule. This latter is pierced before its insertion into the inhaler. A cup is provided for preventing escape of the finely divided medicament through the capsule holes (42, 44) until the moment in which the inhaler is used.

16 Claims, 1 Drawing Sheet

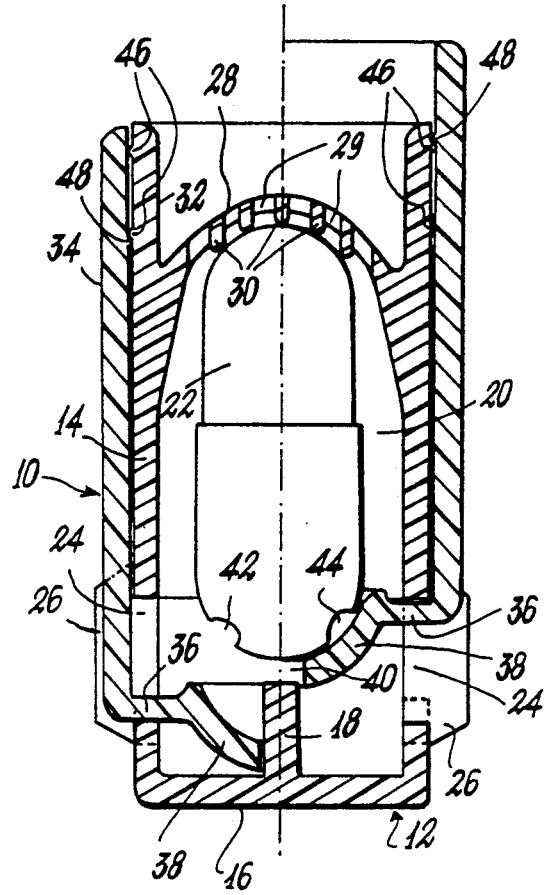

DISPOSABLE INHALER WITH PRE-PIERCED CAPSULE

The present application is a continuation of U.S. Ser. No. 479,273, filed Feb. 13, 1990, now abandoned.

BACKGROUND OF THE INVENTION

1. Field of the Invention

This invention relates to inhalers, i.e., those devices for administering, by inhalation, medicaments in finely divided form contained in capsules.

2. Description of Related Art

In particular, reference should be made to the inhaler described in U.S. Pat. No. 4,069,819, one of the two inventors of which is also one of the two inventors of the present invention. Said patent describes an inhaler of overall cylindrical shape comprising a body enclosing an axially extending nebulization chamber. A capsule containing the medicament in finely divided form is placed in the chamber. The capsules of this type have an overall cylindrical shape with their two ends each having the shape of a spherical cap. The nebulization chamber is of overall cylindrical shape and has a substantially larger cross-section than the cross-section of the capsule to be placed in the chamber. This latter communicates with the outside through air inlet apertures in the chamber wall at or in proximity to one end of the chamber and shaped to generate a swirling air flow through the chamber during inhalation. The chamber also communicates with the outside through air discharge apertures provided in the other spherical cap-shaped end of the chamber and opening into an axial discharge duct. The inhaler is also provided with a piercing device for piercing the casing of the capsule which has previously been inserted into the nebulization chamber. The piercing device is arranged to produce two or more holes in that spherical cap-shaped end of the capsule facing the air inlet apertures.

When the capsule has been pierced, the user brings inhaler up to his nostril or mouth and breathes in. On breathing in, the particular arrangement of the air inlet holes generates within the nebulization chamber a swirling air flow which causes the pierced capsule to undergo such movements as to cause the medicament in finely divided form to escape through its holes, so that the powder is entrained outwards by said air flow. The powder passes through said discharge apertures and flows along the subsequent discharge duct until it reaches either the oral cavity or the nasal cavity of the patient, as the case may be.

However, the aforesaid inhaler has certain drawbacks. In this respect it has been found that in a large number of cases the emptying of the capsule is irregular and incomplete, with consequent difficulties in administering the finely divided medicament.

This drawback is obviated by the invention described in the patent application entitled INHALER WITH REGULAR COMPLETE EMPTYING OF THE CAPSULE in the name of the proprietor of the present patent application and filed on the same date as the present application (i.e., now U.S. Pat. No. 4,995,385). It describes how the nebulization chamber has to be constructed to ensure emptying of the capsule containing the medicament in finely divided form. Specifically, said patent application describes by way of example an embodiment of a disposable inhaler, into which the capsule is inserted during the assembly of the various component pieces of the inhaler. A piercing device enables the capsule to be pierced on use.

An examination of the drawings of said patent application, which illustrate the said disposable inhaler, shows that it is still of rather complex structure as it has to also comprise said capsule piercing device.

SUMMARY OF THE INVENTION

The object of the present invention is to substantially simplify the structure of disposable inhalers of the aforesaid type. Said object is attained by the disposable inhaler according to the present invention, in which the capsule containing the medicament in finely divided form is inserted into the nebulization chamber during assembly of the component parts of the inhaler, characterised in that the inhaler does not possess a capsule piercing device, the capsule being pierced before being inserted into the inhaler. The inhaler of the present invention also includes means for preventing escape of the finely divided medicament through the holes of the pre-pierced capsule until the moment in which the inhaler is used.

It is apparent that as the piercing device has been eliminated, the inhaler structure is considerably simplified, thus very favourably affecting its cost. This is particularly important in the light of the fact that the inhaler is of disposable type, i.e., discarded when used.

Conveniently, the means for preventing escape of the medicament through the capsule holes consist of a cup which embraces the terminal spherical cap-shaped part of the capsule in which the holes have been previously formed, so closing them; said cup being retractable to open the holes at the moment of use of the inhaler.

BRIEF DESCRIPTION OF THE DRAWINGS

The invention will be more apparent from the description of some embodiments thereof given hereinafter by way of example only. In said description reference is made to the accompanying drawings in which:

FIG. 1 is an axial longitudinal section through a first embodiment of a disposable inhaler according to the invention, ready to be used by axially squeezing it, the right half of the figure showing the inhaler as sold (i.e., packaged, not immediately ready for use, whereas the left half of the figure shows it ready for use;

FIG. 2 is an axial longitudinal section through a second embodiment of the invention ready to be used by once traction has been applied, the right half of the figure again showing the inhaler as sold (i.e., packaged, not immediately ready for use); and FIG. 3. is an axial longitudinal section through a third embodiment of the invention of the type used by once traction has been applied, the left half of the figure showing the inhaler ready for use and the right half of the figure showing the inhaler as sold (i.e., packaged, not immediately ready for use).

DESCRIPTION OF THE PREFERRED EMBODIMENTS

From FIG. 1 it can be seen that the disposable inhaler 10 comprises a body 12 of overall cylindrical shape comprising a tubular side wall 14 and a base wall 16, fixed to the tubular wall 14. A coaxial cylindrical element 18 extends upwards from the base wall 16. The body 12 encloses a nebulization chamber 20 arranged to receive an ovoid capsule 22 of well known type containing the medicament in finely divided form to be administered by inhalation. The nebulization chamber 20 can be made to communicate with the outside through the air inlet slits 24 provided in the side wall 14 of the cylindrical body 12. For simplicity, the figures show only those slits corresponding with the section plane. These are of the type described in U.S. Pat. No. 4,069,819 (to which reference should be made), these slits also being externally delimited by fins 26 of the type described in the said copending patent application (now U.S. Pat. No. 4,995,385) said copending patent application.

The lower portion of the nebulization chamber has a cylindrical shape and the upper portion of the nebulization chamber is upperly tapered to connect to a perforated baffle 28 of dome shape. The inner surface of the perforated baffle 28 includes pegs 30 which project downwardly parallel to the axis of the inhaler 10, their purpose being as explained in the aforesaid copending patent application (e.g., at column 4, lines 12 to 19 of U.S. Pat. No. 4,995,385—i.e., to prevent the capsule 22 from blocking the flow of the medicament out the discharge channel 32). The remaining upper part of the body 12 forms a discharge channel 32 for the air laden with the medicament in finely divided form. An operating sleeve 34 provided with a certain number of spokes 36 extending inwards through said slits 24 can slide in both directions on the outer surface of the cylindrical body 12. To the inner end of said spokes 36 there is fixed a coaxial cup 38 having a coaxial hole 40 through which the cylindrical element 18 can slide. The cup 38 has a shape which mates with the shape of the spherical cap end of the pre-pierced capsule 22. When the cup 38 is in the position shown to the right of FIG. 1, it closes the holes 42, 44 in the capsules 22 to prevent the medicament in finely divided form contained in the capsule 22 from escaping through said holes. The cup 38 can move together with the operating sleeve 34, the travel of which is limited by the presence of the spokes 36 which slide in the slits 24.

Consequently by moving the sleeve 34 the cup 38 is able to move between the two outer positions shown in FIG. 1, the position shown to the right (corresponding to the position of the cup 38 at the time of sale of the inhaler—the cup 38 closing the holes 42, 44 in the capsule 22), whereas the position shown to the left is that in which the inhaler is ready for use. In reality, in FIG. 1 the capsule 22 is shown in the situation corresponding to the upper end position of the sleeve 34 and thus of the cup 38, the true position which the capsule assumes when the sleeve is in its lower end position not being shown for simplicity (i.e., capsule 22 would slide down and rattle around within the nebulization chamber 20, as per U.S. Pat. No. 4,995,385).

Suitable means are provided to prevent undesired movement of the sleeve 34 and to lock it in the position for use. As the inhaler is usually of plastic material, said means can for example consist of transverse ribs 46 and 48 provided on the outer lateral surface of the body 12 and on the corresponding inner lateral surface of the sleeve 34 respectively. These ribs project from the relative surface in such a manner as to mutually interfere, so that to move the sleeve 34 from one of its two end positions it is necessary for the rib 48 of the sleeve 34 to pass over the relative rib 46 of the body 12. Other means can obviously be used to obtain the same result, such as the elastic tongues 47, 49 shown in FIG. 3, the purpose of which is to lock the cup 38 in the position for use.

As is apparent, to use the inhaler of FIG. 1 it is necessary only to exert an axial squeezing action on it to withdraw the cup 38 from the perforated base of the capsule 22. After that, inhalation can proceed. To ensure separation of the capsule 22 from the cup 38 an extractor means 18 is provided which (when the inhaler is ready for inhalation keeps the capsule in the optimum position for initiating its precession movement (i.e., movement with at least two degress of freedom) as soon as inhalation commences. For a description of the manner in which the capsule moves during inhalation reference should be made to the aforesaid copending patent application (now U.S. Pat. No. 4,995,385).

FIG. 2 shows a modification of the disposable inhaler according to the invention in which those parts which remain identical to those of FIG. 1 are indicated by the same reference numerals. The only substantial difference compared with the embodiment of FIG. 1 is that, to arrange the inhaler 50 for use, a pulling action must be exerted on it. More precisely, the sleeve 54, which extends downwards from the spokes 36, has a greater diameter than the sleeve of FIG. 1 because it has to slide over the fins 26 of the cylindrical body 12. To arrange the inhaler 50 for use it is necessary only to grip both the lateral surface of the body 12 and the lateral surface of the sleeve 54 with the fingers and axially pull them apart until they stop. Again in this case suitable means can be provided to ensure that a certain force is required to move the sleeve from its end positions, as in the case of the inhaler 10 of FIG. 1, or means for locking the cup in its lower end position, as in the case of the inhaler 60 of FIG. 3. If the inhaler is of the type for applying to a nostril it will have a narrower air discharge duct than those shown in FIGS. 1 and 2 (which are intended to administer medicaments orally). The modified embodiment shown in FIG. 3 represents an inhaler of this type, which is otherwise substantially identical to that of FIG. 2, the modification obviously also being applicable to the inhalers of FIGS. 1 and 2.

In the case of FIGS. 2 and 3, suitable knurling can be applied to the lateral surface of the body 12 and sleeve 54 to facilitate gripping.

In all the aforedescribed embodiments of the inhaler according to the invention it is necessary for the cylindrical body 12 to be constructed in at least two pieces, one of which for example forms the upper part of the lateral wall 14 as far as the lower edge of the slits 24, and the other forms the base wall 16 with the relative remaining part of the lateral wall 14. The two pieces are then joined together by gluing, ultrasonic welding or similar fixing methods.

However, before doing this the cup 38 must be placed inside the nebulization chamber 20 by inserting the appropriate spokes 36 into the corresponding slits 24 (which are still open at their bottom). In the illustrated embodiments, the cup can be in the form of a substantially elastic membrane fixed to the spokes, this providing excellent closure of the capsule holes when the membrane is in its upper position. The embodiment comprising the membrane can be formed either by simply making the cup with fairly thin walls or by gluing a suitable membrane to a ring carried by said spokes.

In all the illustrated embodiments the spokes which support the cup and connect it to the external operating sleeve pass through the slits through which air enters the nebulization chamber. Alternatively, however, these spokes can instead pass through separate apertures provided for this purpose in the lateral wall of the cylindrical body. The cup 38 also functions as a centering means for the pre-pierced capsule 22, which after insertion into the nebulization chamber 20 will not necessarily lie coaxially therein. For this purpose the cup 38 has its upper edge conveniently flared to facilitate centering of the capsule when the cup is moved into the position in which it closes the capsule holes.

Besides its use in administering common medicaments by inhalation, the inhaler according to the invention has proved particularly useful in administering calcitonin, parathyroid hormone and gonadorelin, each of which may be dispersed and administered within mannitol or other suitable vehicles.

What is claimed is:

1. A disposable inhaler (10, 50, 60) for administering medicaments in finely divided form, said medicaments being contained in a capsule (22), said capsule being pierced before being inserted in said inhaler, said inhaler comprising a body (12) enclosing a nebulization chamber (20) and means (38) for preventing escape of said finely divided medicament from said pre-pierced capsule (22) until said inhaler is used, said means for preventing escape being movable from a first position wherein said medicament is prevented from escaping from said pre-pierced capsule (22) and a second position wherein said inhaler is ready for use, wherein said nebulization chamber (20) is dimensioned with respect to said capsule (22) such that, after insertion within said chamber (20), said capsule (22) is movable with at least two degrees of freedom when said means for preventing excape (38) is in said second position, said nebulization chamber being adapted for insertion therein of the capsule during assembly of the inhaler, characterized in that said nebulization chamber is substantially smooth and in that the inhaler does not possess means for rupturing the capsule, whereby the regular precession movement of the capsule within the nebulization chamber as air is drawn therethrough is not impeded and whereby, as air is drawn through said nebulization chamber, said capsule is not in contact with any part of said nebulization chamber a substantial portion of the time.

2. The disposable inhaler as claimed in claim 1, wherein the means (38) for preventing escape of the finely divided medicament from said pre-pierced capsule (22) includes a cup (38) which embraces the portion of the capsule which has been pierced before being inserted into the nebulization chamber (20) of said inhaler, whereby the medicament is substantially prevented from exiting the capsule, said cup being retractable to permit said medicament to exit said pre-pierced capsule at the moment of use of the inhaler.

3. The disposable inhaler as claimed in claim 1 further comprising an external sleeve (34) slidably positioned around the body (12) of said inhaler so as to be slidable along the longitudinal axis of the body (12), said body (12) including apertures (24), said external sleeve (34) further including inwardly-directed spokes (36) passing through said apertures (24) in said body (12), said cup (38) being fixed to the spokes (36), said spokes (36) being provided for moving said cup (38) vertically, whereby the medicament may be prevented from exiting said pre-pieced capsule when said cup (38) is raised or allowed to exit said pre-pierced capsule and said inhaler when said cup (38) is retracted.

4. The disposable inhaler as claimed in claim 3 further comprising an extractor means (18) for ensuring that the capsule (22) separates from said cup (38) when it is desired to allow the escape of the medicament from the capsule.

5. The disposable inhaler as claimed in claim 4 further comprising means for preventing undesired movement of the sleeve (34) whereby said sleeve may be locked in a position for allowing said medicament to escape from said pre-pierced capsule.

6. The disposable inhaler as claimed in claim 2 further comprising an external sleeve (34) slidably positioned around the body (12) of said inhaler so as to be slidable along the longitudinal axis of the body (12), said body (12) including apertures (24), said external sleeve (34) further including inwardly-directed spokes (36) passing through said apertures (24) in said body (12), said cup (38) being fixed to the spokes (36), said spokes (36) being provided for moving said cup (38) vertically, whereby the medicament may be prevented from exiting said pre-pierced capsule when said cup (38) is raised or allowed to exit said pre-pierced capsule and said inhaler when said cup (38) is retracted 7. The disposable inhaler as claimed in claim 6 further comprising an extractor means (18) for ensuring that the capsule (22) separates from said cup (38) when it is desired to allow the escape of the medicament from the capsule.

8. The disposable inhaler as claimed in claim 7 further comprising means for preventing undesired movement of the sleeve (34) whereby said sleeve may be locked in a position for allowing said medicament to escape from said pre-pierced capsule.

9. A disposable inhaler for administering medicaments in finely divided form, comprising:
   (a) a capsule for containing said medicaments, said capsule being pre-pierced;
   (b) a body, said body have a nebulization chamber adapted to hold said capsule, said nebulization chamber being substantially smooth and lacking means to rupture said capsule; and
   (c) means for preventing the escape of said finely divided medicament from said capsule until said inhaler is used,
   wherein said means for preventing escape of said finely divided medicament from said pre-pierced capsule until said inhaler is used are movable from a first position wherein said medicament is prevented from escaping from said pre-pierced capsule and a second position wherein said inhaler is ready for use, wherein said nebulization chamber is dimensioned with respect to said capsule such that, after insertion within said chamber, said capsule is movable with at least two degrees of freedom when said means for preventing escape is in said second position.

10. A disposable inhaler (10, 50, 60) for administering medicaments in finely divided form, said medicaments being contained in a capsule (22), said inhaler comprising a body (12) enclosing a nebulization chamber (20), said nebulization chamber being adapted for insertion therein of the capsule during assembly of the inhaler, characterized in that said nebulization chamber is substantially smooth and in that the inhaler does not possess means for rupturing the capsule, whereby the regular precession movement of the capsule within the nebulization chamber as air is drawn therethrough is not impeded, and characterized in that said capsule is pierced before being inserted into the inhaler, said inhaler further comprising means (38) for preventing escape of the finely divided medicament from said pre-pierced capsule until the moment at which the inhaler is used;

said disposable inhaler further comprising an external sleeve (34) slidably positioned around the body (12) of said inhaler so as to be slidable along the longitudinal axis of the body (12), said body (12) including apertures (24), said external sleeve (34) further including inwardly-directed spokes (36) passing through said apertures (24) in said body (12), said cup (38) being fixed to the spokes (36), said spokes (36) being provided for moving said cup (38) vertically, whereby the medicament may be prevented from exiting said pre-pierced capsule when said cup (38) is raised or allowed to exit said pre-pierced capsule and said inhaler when said cup (38) is retracted.

11. A disposable inhaler (10, 50, 60) for administering medicaments in finely divided form, said medicaments being contained in a capsule (22), said inhaler comprising a body (12) enclosing a nebulization chamber (20), said nebulization chamber being adapted for insertion therein of the capsule during assembly of the inhaler, characterized in that said nebulization chamber is substantially smooth and in that the inhaler does not possess means for rupturing the capsule, wherby the regular precession movement of the capsule within the nebulization chamber as air is drawn therethrough is not impeded and whereby, as air is drawn through said nebulization chamber said capsule is not in contact with any part of said nebulization chamber a substantial portion of time, and characterized in that said capsule is pierced before being inserted into the inhaler, said inhaler further comprising means (38) for preventing escape of the finely divided medicament from said pre-pierced capsule until the moment at which the inhaler is used;
   wherein the means (38) for preventing escape of the finely divided medicament from said pre-pierced capsule (22) includes a cup (38) which embraces the portion of the capsule which has been pierced before being inserted into the nebulization chamber (20) of said inhaler, whereby the medicament is substantially prevented from exiting the capsule, said cup being retractable to permit said medicament to exit said pre-pierced capsule at the moment of use of the inhaler;
   said disposable inhaler further comprising an external sleeve (34) slidably positioned around the body (12) of said inhaler so as to be slidable along the longitudinal axis of the body (12), said body (12) including apertures (24), said external sleeve (34) further including inwardly-directed spokes (36) passing through said apertures (24) in said body (12), said cup (38) being fixed to the spokes (36), said spokes (36) being provided for moving said cup (38) vertically, whereby the medicament may be prevented from exiting said pre-pierced capsule when said cup (38) is raised or allowed to exit said pre-pierced capsule and said inhaler when said cup (38) is retracted.

12. The disposable inhaler as claimed in claim 11 further comprising an extractor means (18) for ensuring that the capsule (22) separates from said cup (38) when it is desired to allow the escape of the medicament from the capsule.

13. The disposable inhaler as claimed in claim 12 further comprising means for preventing undesired movement of the sleeve (34) whereby said sleeve may be locked in a position for allowing said medicament to escape from said pre-pierced capsule.

14. A disposable inhaler (10, 50, 60) for administering medicaments in finely divided form, said medicaments being contained in a capsule (22), said inhaler comprising a body (12) enclosing a nebulization chamber (20), said nebulization chamber being adapted for insertion therein of the capsule during assembly of the inhaler, characterized in that said nebulization chamber is substantially smooth and in that the inhaler does not possess means for rupturing the capsule, whereby the regular precession movement of the capsule within the nebulization chamber as air is drawn therefore is not impeded and whereby, as air is drawn through said nebulization chamber, said capsule is not in contact with any part of said nebulization chamber a substantial portion of time, and characterized in that said capsule is pierced before being inserted into the inhaler, said inhaler further comprising means (38) for preventing escape of the finely divided medicament from said pre-pierced capsule until the moment at which the inhaler is used;
   said disposable inhaler further comprising an external sleeve (34) slidably positioned around the body (12) of the said inhaler so as to be slidable along the longitudinal axis of the body (12), said body (12) including apertures (24), said external sleeve (34) further including inwardly-directed spokes (36) passing through said apertures (24) in said body (12), said cup (38) being fixed tp the spokes (36) said spokes (36) being provided for moving said cup (38) vertically, whereby the medicament may be prevented from exiting said pre-pierced capsule when said cup (38) is raised or allowed to exit said pre-pierced capsule and said inhaler when said cup (38) is retracted.

15. The disposable inhaler as claimed in claim 14 further comprising an extractor means (18) for ensuring that the capsule (22) separates from said cup (38) when it is desired to allow the escape of the medicament from the capsule.

16. The disposable inhaler as claimed in claim 15 further comprising means for preventing undesired movement of the sleeve (34) whereby said sleeve may be locked in a position for allowing said medicament to escape from said pre-pierced capsule.

* * * * *